United States Patent [19]

Montle et al.

[11] 4,323,690
[45] Apr. 6, 1982

[54] METHOD OF MAKING SILICATE ESTERS

[75] Inventors: John F. Montle, St. Louis; Henry J. Markowski, Manchester; Paul D. Lodewyck, St. Louis; Daniel F. Schneider, III, House Springs, all of Mo.

[73] Assignee: Carboline Company, St. Louis, Mo.

[21] Appl. No.: 255,479

[22] Filed: Apr. 20, 1981

[51] Int. Cl.$^3$ .............................. C07F 7/04; C07F 7/18
[52] U.S. Cl. .................................. 556/470; 556/446; 252/431 C; 252/476
[58] Field of Search ............................... 556/446, 470

[56] References Cited

U.S. PATENT DOCUMENTS

| 2,473,260 | 6/1949 | Rochow. | |
|---|---|---|---|
| 3,232,972 | 2/1966 | Beanland | 556/470 |
| 3,557,179 | 1/1971 | Lenz et al. . | |
| 3,627,807 | 12/1971 | Bleh et al. . | |
| 3,641,077 | 2/1972 | Rochow . | |
| 3,803,197 | 4/1974 | Anderson et al. . | |
| 4,113,761 | 9/1978 | Kreuzburg et al. . | |
| 4,185,029 | 1/1980 | Kreuzburg et al. . | |
| 4,211,717 | 7/1980 | Emblem et al. | 556/470 |

FOREIGN PATENT DOCUMENTS

| 53-76891 | 6/1978 | Japan | 556/470 |
|---|---|---|---|
| 54-149290 | 5/1979 | Japan | 556/470 |

*Primary Examiner*—Paul F. Shaver

[57] ABSTRACT

Tetra-alkyl and tetra-alkoxyalkyl silicates are made by reacting an alkanol or an alkoxyalkanol with silicon in the presence of an alkali metal carboxylic acid salt.

11 Claims, No Drawings

METHOD OF MAKING SILICATE ESTERS

The invention relates to a method for preparing tetraalkyl and tetraalkoxyalkyl silicates from a primary alkanol or alkoxyalkanol and silicon.

The formation of tetraalkyl or tetraalkoxyalkyl silicates by reacting the appropriate alkanol or alkoxyalkanol with silicon in the presence of an alkali alkanolate or alkoxyalkanolate catalyst under various conditions has been described in numerous U.S. Pat. Nos. such as Lenz 3,557,179; and Bleh 3,627,807; Anderson et al. 3,803,197; Kreuzburg et al. 4,113,761; Kreuzburg et al. 4,185,029; and Flick et al. 4,224,234. In addition, Joch et al. 4,197,252 has described carrying out such a reaction in the presence of sodium, while Rochow 2,473,260 and Rochow 3,641,077 have described the use of copper or copper compounds as catalysts for such a reaction.

The difficulty with carrying out the reaction using the corresponding alkali metal alkanolate or alkoxyalkanolate as catalyst, as described for example in Kreuzburg et al. 4,113,761 and 4,185,029 is that side reactions occur in which water and other products are formed. The water is undesirable in that it can react with tetraalkyl silicate, thereby lowering the yield; or it can react with the alkali metal alcoholate to form the corresponding alcohol and alkali metal hydroxide, which is not an effective catalyst for the reaction. (Any water present in the reactants will also react with the alkali metal alcoholate, thereby requiring that "dry" reagents be used, or that additional alkali metal alcoholate be used to compensate for the reduction in activity.)

Surprisingly, it has been discovered that when using an alkali metal carboxylic acid salt as the catalyst, these side reactions are not evident. In addition, the alkali metal carboxylic acid salt does not react with water under the conditions described, therefore its catalytic properties are unaffected by water present when the reactants are charged to the reactor, although any water present will reduce the yield, in that it will react with the tetra-alkyl silicate as it is formed.

It has also been found that the tetraalkyl or tetraalkoxyalkyl silicate products are much more readily separated from the alkali metal carboxylic acid salts than from the alkali metal alkanolates or alkoxides, so that the process of the present invention offers an additional advantage over the prior art.

It has been discovered that tetra-alkyl or -alkoxyalkyl silicates in which each alkyl or alkoxyalkyl group has from 1 to 6 carbon atoms can be easily and simply produced in a single stage in high yields and at a high rate of reaction by heating at a temperature from about 140°–250° C., a mixture of the desired alcohols (alkanols or alkoxyalkanols having 1 to 6 carbon atoms) with finely-divided silicon and an alkali metal carboxylic acid salt, the amount of said salt being equivalent to at least about 0.1% by weight, preferably about 0.4 to 5% by weight, of alkali metal based on the total weight of alcohols, and separating the hydrogen by-product from the reaction mixture. The temperature is maintained at 140° to 250° C. during the reaction with silicon while maintaining the pressure sufficiently high to keep the alcohols in a liquid phase.

In carrying out the process of the present invention in a batch mode the sequence in which the several reagents are introduced into the reaction mixture is not important, but it is convenient to introduce the silicon last.

The alkali metal carboxylic acid salt used in this invention can be any of the carboxylic acid salts of Group I alkali metals, such as: lithium, sodium, potassium, cesium, rubidium. The only limitation is the salt must be soluble to the extent of at least 0.1% by weight of equivalent alkali metal based on the alcohol present in the reaction mixture at 140° C. or higher. The amount of alkali metal is equal to at least 0.1% by weight of the total alcohol present at the beginning of the reaction with the silicon, preferably from 0.4 to 5% by weight. Among the carboxylic acid, alkali metal salts of which can be used as catalysts in the present invention are formic, acetic, propionic and benzoic. The usual industrial grades of alcohol can be used in the present invention. For best results, alcohol of 95% purity or better is employed. Among the alcohols which can be used are methanol, ethanol, 1-propanol, 1-hexanol, 2-methoxyethanol, 2-ethoxyethanol, diethylene glycol monomethyl ether, and diethylene glycol monoethyl ether. Silicon metal can be used in pure form or in the form of such commercially available alloys or mixtures as ferrosilicon or iron silicide containing at least about 33% silicon by weight. If methyl alcohol is used in conjunction with other alcohols, the speed of reaction at a given temperature increases as the proportion of methyl alcohol in the reaction mixture is increased.

The amount of silicon metal employed is not critical, but optimum results are obtained in a batch process when it is used in an amount approximately equal stoichiometrically to the total amount of alcohol present, i.e., the stoichiometric amount ±10%.

Since the reaction with silicon is most rapid at temperatures well above the boiling point of many of the alcohols used, it is generally carried out in a sealed vessel fitted with a condenser with a metering valve to maintain the pressure sufficiently high to keep the alcohols in the liquid phase, e.g., a pressure from 75 to 500 p.s.i.g., and to allow evolved hydrogen gas to escape, the rate of hydrogen gas formation indicating the rate of silicate formation. A pressure of 200 p.s.i.g. will typically be reached in the case of methanol and ethanol when the temperature reaches between 150° and 165° C. The temperature should be kept between 140° and 250° C., and about 4 to 15 hours have been found to be sufficient time for substantial completion of the reaction when carried out as a batch process; it is also possible to carry out the process as a continuous or steady state process in which reagents are continuously introduced into a reaction vessel and products are continually withdrawn. Pressures as high as 500 p.s.i.g. or even higher can be employed if suitable high pressure equipment is used. Pressures of 75 to 300 p.s.i.g. are preferred because less expensive equipment is required. After the reaction is complete the material can then be subjected to distillation to separate the tetraalkyl or tetraalkoxyalkyl silicates from the reaction mixture as well as to separate the silicates from each other when a mixture of alcohols is used, if desired. Residual alkali metal carboxylic acid salt remaining after distillation can be reused as catalyst if desired.

In order to maintain a high rate of reaction between the silicon and the alcohols and to minimize caking of solids, it is desirable to provide effective agitation of the reaction mixture, for example, with an adequate stirrer. It is also possible but not essential, to include a surface active agent which is stable in the reaction media; fluorinated surface active agents such as those sold under the trade name Fluorad, have been found suitable. The time required for the reaction and the yield of product (based on silicon) vary depending upon the identity and relative proportions of the alcohols present. When ethanol and methanol are employed together, the speed of the reaction increases as the amount of methyl alcohol increases, but the product contains a smaller proportion of the tetra-ethyl silicate. When ethanol and alkali metal carboxylic acid salt alone are present, the speed and yield of reaction is somewhat lower than with methanol and the salt alone. When a mixture of equal volumes of ethanol and methanol are used with alkali metal carboxylic acid salt in an amount of about 0.5% by weight of the total alcohols, a yield of 85% of theoretical or more can be obtained in as little as 4 hours.

The following specific examples are intended to illustrate more clearly the nature of the invention without acting as a limitation on its scope. In each example commercially available ferrosilicon (containing 98% silicon) was used as the source of silicon.

EXAMPLE 1

A reaction mixture having the following composition was prepared.

| Materials | % Composition (by weight) |
|---|---|
| Ethanol | 82.8% |
| Potassium Formate | 4.4% |
| Silicon (98% pure) | 12.8% |
| Total | 100.0% |

All ingredients were charged into a pressure reactor having a motor-powered agitating blade and a condenser with a pressure-regulating and gas-releasing valve. Then the pressure vessel's head was attached and sealed, and the heater and agitating blade were activated. As the temperature within the reactor increased to about 180° C., the pressure reached 300 p.s.i.g., and the pressure relief valve was manually adjusted to maintain the pressure at 300–320 p.s.i.g. and release the hydrogen gas formed. After approximately 5 hours, the temperature reached 200° C., the heat was turned off and the pressure was lowered slowly to atmospheric pressure while the reactor cooled.

After the material had cooled, it was drained into a flask and the tetra-ethyl silicate was vacuum distilled at 100° C. A 60% yield of tetra-ethyl silicate was achieved based upon silicon consumed.

EXAMPLE 2

The procedure described in Example 1 was repeated except that the temperature was maintained at 160°–200° C. and the pressure at 200–260 p.s.i.g. for 14 hours, and the composition of the starting materials was as follows:

| Materials | % Composition (by weight) |
|---|---|
| Ethanol | 78.2% |
| Potassium Formate | 9.7% |
| Silicon (98% pure) | 12.1% |
| Total | 100.0% |

In this example, a yield of greater than 73% of tetraethyl silicate was obtained based on the amount of silicon consumed.

EXAMPLE 3

The procedure in Example 1 was repeated except that the temperature was maintained at 160°–230° C. and the pressure at approximately 200 p.s.i.g. for 4 hours, and the composition of the starting materials was as follows:

| Materials | % Composition (by weight) |
|---|---|
| Ethanol | 57.5% |
| Methanol | 23.6% |
| Potassium Formate | 4.8% |
| Silicon (98% pure) | 14.1% |
| Total | 100.0% |

In this example, a yield of 98% of tetra-alkyl silicate, including tetramethyl, tetraethyl, and mixed methyl ethyl silicates, was obtained based on the amount of silicon consumed.

EXAMPLE 4

The procedure as described in Example 1 was followed except that the pressure was maintained at 200 to 250 p.s.i.g. for 8 hours, and the starting composition was as follows:

| Materials | % Composition (by weight) |
|---|---|
| Ethanol | 58.1% |
| Methanol | 23.7% |
| Sodium Formate | 3.9% |
| Silicon (98% pure) | 14.3% |
| Total | 100.0% |

In this example the yield was greater than 88% based on the silicon consumed.

EXAMPLE 5

The procedure of Example 1 was followed except that the pressure was maintained at 200 to 280 p.s.i.g. for approximately 5 hours, and the starting composition was as follows:

| Materials | % Composition (by weight) |
|---|---|
| Ethanol | 41.7% |
| Methanol | 41.5% |
| Sodium Formate | 1.1% |
| Silicon (98% pure) | 15.7% |
| Total | 100.0% |

In this example the yield was greater than 85% based on the silicon consumed.

EXAMPLE 6

The procedure described in Example 1 was repeated except that the temperature was maintained at 140°–175° C. and the pressure at 125 to 150 p.s.i.g. for 13 hours, and the starting composition was as follows:

| Materials | % Composition (by weight) |
|---|---|
| Methanol | 80.0% |
| Sodium Acetate | 2.1% |
| Silicon (98% pure) | 17.9% |
| Total | 100.0% |

In this example the yield was greater than 78%, based on the silicon consumed.

EXAMPLE 7

The procedure described in Example 1 was followed except that the temperature was maintained at 145°–185° C. and the pressure at 170 to 180 p.s.i.g. for 10 hours, and the starting composition was as follows:

| Materials | % Composition (by weight) |
|---|---|
| Methanol | 79.7% |
| Sodium Propionate | 2.5% |
| Silicon (98% pure) | 17.8% |
| Total | 100.0% |

In this example, the yield was approximately 78% based on the silicon consumed.

EXAMPLE 8

The procedure described in Example 1 was repeated except pressure was maintained at 150 to 190 p.s.i.g. for 9 hours and the composition was as follows:

| Materials | % Composition (by weight) |
|---|---|
| Methanol | 80.3% |
| Sodium Formate | 1.8% |
| Silicon (98% pure) | 17.9% |
| Total | 100.0% |

In this example, the yield was greater than 90% based on the silicon consumed.

EXAMPLE 9

The procedure described in Example 1 was repeated using the following starting composition except that the temperature was maintained at 150°–165° C. and the pressure at 200 to 250 p.s.i.g. for 5 hours.

| Materials | % Composition (by weight) |
|---|---|
| Methanol | 78.8% |
| Sodium Benzoate | 3.6% |
| Silicon (98% pure) | 17.6% |
| Total | 100.0% |

The yield was approximately 35% based on silicon consumed.

EXAMPLE 10

The procedure described in Example 1 was repeated except that the temperature was maintained at 150°–190° C. and the pressure at 180 to 260 p.s.i.g. for 15 hours, and the starting composition was as follows:

| Materials | % Composition (by weight) |
|---|---|
| Ethanol | 56.9% |
| Methanol | 23.3% |
| Potassium Acetate | 5.8% |
| Silicon (98% pure) | 14.0% |
| Total | 100.0% |

In this example, the yield was greater than 73% based on silicon consumed.

EXAMPLE 11

The procedure as described in Example 1 was repeated except that the pressure was maintained at 200 p.s.i.g. for 4 hours, and the starting composition was as follows:

| Materials | % Composition (by weight) |
|---|---|
| Ethanol | 52.6% |
| Methanol | 21.6% |
| Potassium Formate | 12.9% |
| Silicon (98% pure) | 12.9% |
| Total | 100.0% |

In this example the yield was greater than 95% based on the silicon consumed.

EXAMPLE 12

The procedure of Example 1 was repeated with the following starting composition except that the temperature was maintained at 165°–200° C. and the pressure at 250 to 260 p.s.i.g. for 4 hours.

| Materials | % Composition (by weight) |
|---|---|
| Ethanol | 41.6% |
| Methanol | 41.5% |
| Sodium Formate | 0.8% |
| Potassium Formate | 0.4% |
| Silicon | 15.7% |
| Total | 100.0% |

The yield was over 86% based on the silicon consumed.

Similar results can be obtained employing various industrial grades of ethanol and methanol or alkoxyalkyl alcohols, etc., and using ferrosilicon or iron silicide in place of silicon.

What is claimed is:

1. A process for making tetraalkyl or tetraalkoxyalkyl silicates comprising heating an alkanol or an alkoxyalkanol having from 1 to 6 carbon atoms with finely divided silicon and with an alkali metal carboxylic acid salt, and separating the hydrogen by-product from the reaction mixture.

2. A process for making tetraethyl silicate comprising heating at a temperature from 140° to 250° C. at elevated pressure ethanol with finely-divided silicon and with an alkali metal carboxylic acid salt, the amount of said alkali metal carboxylic acid salt being equivalent to at least 0.1% by weight of alkali metal based on the total weight of ethanol, and separating the hydrogen by-product from the reaction mixture.

3. The process as claimed in claim 2 in which the amount of said alkali metal carboxylic acid salt is equivalent to 0.4 to 5% by weight of alkali metal based on the total weight of ethanol.

4. A process for making tetraethyl silicate in admixture with tetramethyl and other silicates comprising heating a mixture of ethanol and methanol with finely-divided silicon and with a alkali metal carboxylic acid salt at a temperature from 140° to 250° C. at elevated pressure, the amount of said salt being equivalent to at least 0.1% by weight of alkali metal based on the total weight of alcohols, and separating the hydrogen by-product from the reaction mixture.

5. The process as claimed in claim 4 in which the amount of alkali metal carboxylic acid salt is equivalent to 0.4 to 5% by weight of alkali metal based on the total weight of alcohols.

6. The process as claimed in any of claims 1, 2, 3, 4 or 5 in which said silicon is employed in an amount approximately stoichiometrically equal to the total amount of alcohol present.

7. The process as claimed in any of claims 1, 2, 3, 4 or 5 in which said alkali metal is sodium.

8. The process as claimed in any of claims 1, 2, 3, 4 or 5 in which alkali metal carboxylic acid salt is sodium formate.

9. The process as claimed in any of claims 1, 2, 3, 4 or 5 in which said alkali metal is potassium.

10. The process as claimed in any of claims 1, 2, 3, 4 or 5 in which said alkali metal carboxylic acid salt is potassium formate.

11. The process as claimed in any of claims 1, 2, 3, 4 or 5 in which the silicon is present as Ferrosilicon.

* * * * *